United States Patent
Meidler et al.

(10) Patent No.: US 9,328,338 B2
(45) Date of Patent: May 3, 2016

(54) METHOD FOR REMOVING A LYTIC ENZYME FROM A HETEROGENEOUS MIXTURE

(75) Inventors: Roberto Meidler, Rehovot (IL); Nina Raver-Shapira, Ramot Meir (IL); Liliana Bar, Rehovot (IL); Oleg Belyaev, Petah Tikva (IL); Israel Nur, Moshav Timmorim (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 0 days.

(21) Appl. No.: 13/532,997

(22) Filed: Jun. 26, 2012

(65) Prior Publication Data

US 2013/0005947 A1 Jan. 3, 2013

Related U.S. Application Data

(60) Provisional application No. 61/502,905, filed on Jun. 30, 2011.

(30) Foreign Application Priority Data

Jun. 30, 2011 (IL) .......................................... 213864

(51) Int. Cl.
| | | |
|---|---|---|
| *C12N 9/50* | (2006.01) | |
| *C07K 14/81* | (2006.01) | |
| *C12N 9/68* | (2006.01) | |
| *C07K 1/22* | (2006.01) | |

(52) U.S. Cl.
CPC ... *C12N 9/50* (2013.01); *C07K 1/22* (2013.01); *C07K 14/81* (2013.01); *C07K 14/811* (2013.01); *C12N 9/6435* (2013.01); *C12Y 304/21007* (2013.01)

(58) Field of Classification Search
None
See application file for complete search history.

(56) References Cited

U.S. PATENT DOCUMENTS

| | | | |
|---|---|---|---|
| 4,188,318 A * | 2/1980 | Shanbrom ..................... | 530/383 |
| 4,297,344 A | 10/1981 | Schwinn et al. | |
| 4,341,764 A | 7/1982 | Wallace et al. | |
| 4,455,300 A * | 6/1984 | Wallace et al. ................ | 514/9.3 |
| 6,815,535 B1 | 11/2004 | Kanellos et al. | |
| 7,125,569 B2 | 10/2006 | Nur et al. | |
| 2005/0197493 A1* | 9/2005 | Metzner et al. ............... | 530/383 |
| 2009/0018313 A1* | 1/2009 | Shanbrom ..................... | 530/382 |

FOREIGN PATENT DOCUMENTS

| | | |
|---|---|---|
| DE | 204944 | 12/1983 |
| EP | 1390485 | 10/2006 |
| GB | 1480867 | 7/1977 |
| WO | WO 93/05822 | 4/1993 |
| WO | WO 94/22503 | 10/1994 |
| WO | WO 02/095019 | * 11/2002 |

OTHER PUBLICATIONS

Definition of heterogeneous from chemistry.about.com < http://chemistry.about.com/od/chemistryglossary/g/Heterogeneous-Mixture-Definition.htm > Retrieved Apr. 8, 2015.*
Clauss V.A. 'Gerinnungsphysiologische Schnellmethode zur Bestimmung des Fibrinogens' Acta Haematol. (1957) vol. 17 pp. 237-246.—In German.
Ersson, B. et al *Intro to Protein Purification; Protein Purification: Principles, High Resolution Methods, and Applications* (2011) Third Edition John Wiley & Sons, Inc. pp. 3-22.
Definition of heterogeneous from chemistry.about.com <http://chemistry.about.com/od/chemistryglossary/g/Heterogeneous-Mixture-Definition.htm> Retrieved Apr. 8, 2015.
European Pharmacopaiea, Fibrin sealant kit. (1997) 0903: pp. 857-858.
Guerrier L et al. 'Specific sorbent to remove solvent-detergent mixtures from virus-inactivated biological fluids' Journal of Chromatography B: Biomedical Applications (1995) vol. 664 pp. 119-125.
Haukanes, B.I. et al 'Application of Magnetic Beads in Bioassays' Bio/Technology vol. 11 pp. 60-63 (1993).
Hermanson et al. Immobilized Affinity Ligand Techniques (Academic Press Inc. 1992).
Iwamoto, M. 'Plasminogen-Plasmin System IX. Specific Binding of Tranexamic Acid to Plasmin' Thrombosis et Diathesis Haemorrhagica XX vol. 33, No. 3 (1975) pp. 573-585.
Practical Protein Chromatography edited by Kenney and Fowell vol. 11 Humana Press, 1992.
Roe, S. *Protein Purification Techniques* (2001) Second Edition Oxford University Press pp. 17-23.
Thommes, J. 'Fluidized Bed Adsorption as a Primary Recovery Step in Protein Purification' *Advances in Biochemical Engineering Biotechnology* (1997) vol. 58 Springer-VerlagBerlin Heidelberg pp. 186-230.
International Preliminary Report re: PCT/IL2012/000258 dated Jan. 7, 2014.
International Search Report re:PCT/IL2012/000258 dated Oct. 24, 2012.

* cited by examiner

*Primary Examiner* — Suzanne M Noakes (57) ABSTRACT

The invention relates to purification of an intact, non-degraded macromolecule from a biological mixture comprising the macromolecule in the presence of its lytic enzyme. The method comprises providing the biological mixture as a heterogeneous mixture comprising the lytic enzyme, at least partially, in soluble form and the macromolecule, at least partially, in non-soluble form; batch-wise contacting the heterogeneous mixture with an immobilized inhibitor of the lytic enzyme; increasing the solubility of the macromolecule in the mixture; and removing the immobilized inhibitor from the mixture.

15 Claims, 2 Drawing Sheets

METHOD FOR REMOVING A LYTIC ENZYME FROM A HETEROGENEOUS MIXTURE

FIELD OF THE INVENTION

The invention relates to purification of a macromolecule of interest in its intact, non-degraded form from a mixture comprising said macromolecule in the presence of a lytic enzyme.

BACKGROUND OF THE INVENTION

Typically, purification of intact, non-degraded macromolecules from biological mixtures is difficult due to the presence of lytic enzymes in these mixtures. The presence of lytic enzymes affects the stability of the macromolecule in the biological mixture by causing its degradation. Thus, rapid neutralization of the lytic enzyme at an early step in the purification process is beneficial for increasing the yield and quality (e.g. homogeneity, intactness, and/or functionality) of the purified macromolecule.

The purification is further complicated where the mixture comprising the macromolecule is heterogeneous (i.e. comprises solid particles e.g. particles precipitated in an aqueous solution) and thus cannot be subjected to a purification process in which the mixture is passed at a certain flow rate through a column comprising a packed resin (referred herein as "column purification") without adding preceding steps e.g. solubilization of the particles, dialysis, filtration and/or the like to obtain a clear solution.

Adding such preceding steps for removing the solid particles from the mixture can be time-consuming and expensive and can also undesirably remove the macromolecule of interest, consequently resulting in a low yield of the purified macromolecule.

For example, purification of fibrinogen in its intact non-degraded form from an aluminum hydroxide precipitate [a byproduct from the manufacture process of factor VIII (FVIII)] is compromised by the presence of a high level of the lytic enzyme plasmin and/or plasminogen present in the precipitate.

U.S. Pat. No. 6,815,535 discloses a method for obtaining a fibrinogen enriched preparation e.g. from heparin precipitated paste, a byproduct from the manufacturing process of FVIII. The method includes adding an effective amount of a sulphated polysaccharide (SPS) to a fibrinogen containing solution to form a fibrinogen containing precipitate; and extracting fibrinogen from the fibrinogen containing precipitate with a solution containing NaCl and ε-aminocaproic acid, a soluble inhibitor of the proteolytic enzyme plasmin/plasminogen.

U.S. Pat. No. 7,125,569 discloses the removal of plasmin/plasminogen from a homogenous/clear mixture using a column packed with immobilized tranexamic acid. U.S. Pat. Nos. 4,341,764 and 4,455,300 disclose different byproduct fractions during the manufacturing of FVIII, e.g. aluminum hydroxide residual fraction, which can be used for the purification of fibronectin and fibrinogen.

There is a need for a fast and effective method for purifying a macromolecule of interest in its intact, non-degraded form from a mixture comprising said macromolecule in the presence of lytic enzymes.

SUMMARY OF THE INVENTION

The present invention relates to an effective method for purifying a macromolecule of interest in its intact, non-degraded form from a mixture comprising said macromolecule in the presence of a lytic enzyme.

The purified macromolecule can be obtained as a result of neutralization and removal of the lytic enzyme from the mixture at an early stage in the purification steps.

Thus, the invention also relates to a method for an efficient neutralization and fast removal of a lytic enzyme present in a biological mixture, the mixture comprising the lytic enzyme and a macromolecule of interest that is sensitive to degradation by the lytic enzyme.

In one aspect, the invention relates to a method for removing a lytic enzyme from a biological mixture comprising the lytic enzyme and a macromolecule of interest that is sensitive to the lytic enzyme, the method comprising the steps of: providing the biological mixture as a heterogeneous mixture comprising the lytic enzyme, at least partially, in soluble form and the macromolecule, at least partially, in non-soluble form; providing an inhibitor of the lytic enzyme immobilized on a carrier; contacting the heterogeneous mixture with the immobilized inhibitor in batch form; increasing the solubility of the macromolecule in the mixture; and separating the immobilized inhibitor from the mixture.

In one embodiment of the invention, the biological mixture comprises a cell fraction selected from the group consisting of a platelet extract; an animal tissue extract; an animal bone extract; a gelatin or collagen enriched mixture from animal source; a bovine serum albumin enriched mixture; an animal derived water immiscible fat; a cell culture extract; or a cell culture exudate.

In another embodiment of the invention, the biological mixture is or derives from a body fluid selected from the group consisting of semen, sputum, urine, feces, sweat, saliva, nasal mucus, cerebrospinal fluid, and a blood fraction.

In another embodiment of the invention, the biological mixture is a protein precipitate.

In another further embodiment of the invention, the protein precipitate is a cryoprecipitate.

Yet, in another embodiment of the invention, the protein precipitate is a by-product of the manufacture process of factor VIII and is selected from the group consisting of acid-precipitate, chill-precipitate, aluminum hydroxide precipitate, glycine precipitate, ethanol precipitate, and heparin precipitated paste.

Yet, in another further embodiment of the invention, the protein precipitate is an aluminum hydroxide precipitate.

In one embodiment of the invention, the macromolecule is a protein.

In another embodiment of the invention, the lytic enzyme is a protease.

In another further embodiment of the invention, the inhibitor is an amino acid analog. Yet, in another further embodiment of the invention, the macromolecule is fibrinogen, the lytic enzyme is plasmin and/or plasminogen, and the inhibitor is a lysine analog. In one embodiment of the invention, the lysine analog is tranexamic acid.

In another embodiment of the invention, the heterogeneous mixture is prepared by providing a protein precipitate; and suspending the precipitate with an aqueous solution under conditions that delay solubilization of the macromolecule and/or augment the solubilization of the lytic enzyme.

In another embodiment of the invention, the conditions are selected from the group consisting of a pH range of 7.2-7.3, a temperature range of 30-32° C., an ethanol concentration in the range of 0.2 to 5%, and a combination thereof.

In another embodiment of the invention, the conditions comprise a pH range of 7.2-7.3, a temperature range of 30-32° C., and an ethanol concentration in the range of 0.2 to 5%.

In another embodiment of the invention, the protein precipitate is provided frozen.

In another embodiment of the invention, the method further comprises the step of reducing the mean particle size of the frozen precipitate to about 2-8 mm prior to the suspending.

In one embodiment of the invention, the reduction in the mean particle size is carried out mechanically.

In one embodiment of the invention, the reduction in the mean particle size is carried out using a blender machine.

In another embodiment of the invention, the contacting step is carried out for more than 30 minutes.

In another embodiment of the invention, contacting the heterogeneous mixture with the immobilized inhibitor is carried out for 90 minutes.

In another embodiment of the invention, the separating step is carried out by centrifugation and/or filtration.

In another aspect, the invention relates to a method for removing a lytic enzyme from a precipitated biological mixture comprising the lytic enzyme and a macromolecule of interest that is sensitive to the lytic enzyme, the method comprising the steps of: providing the precipitated biological mixture; providing an inhibitor of the lytic enzyme immobilized on a carrier; partially dissolving the precipitated biological mixture with an aqueous solution to obtain a heterogeneous mixture comprising solid particles comprising the macromolecule; contacting the heterogeneous mixture with the immobilized inhibitor in batch form; dissolving the solid particles in the mixture; and separating the immobilized inhibitor from the mixture.

In one embodiment of the invention, the precipitated biological mixture derives from a body fluid selected from the group consisting of semen, sputum, urine, feces, sweat, saliva, nasal mucus, cerebrospinal fluid, and a blood fraction.

In another embodiment of the invention, the precipitated biological mixture is a protein precipitate.

In a further embodiment, the protein precipitate is a cryoprecipitate.

Yet in another embodiment of the invention, the precipitated biological mixture is a by-product precipitate from the manufacture process of factor VIII and is selected from the group consisting of acid-precipitate, chill-precipitate, aluminum hydroxide precipitate, glycine precipitate, ethanol precipitate, and heparin precipitated paste.

Yet in another further embodiment of the invention, the precipitate is an aluminum hydroxide precipitate.

In another embodiment of the invention, the macromolecule is a protein.

In another embodiment of the invention, the lytic enzyme is a protease.

In a further embodiment, the inhibitor is an amino acid analog.

In one embodiment of the invention, the macromolecule is fibrinogen, the lytic enzyme is plasmin and/or plasminogen, and the inhibitor is a lysine analog.

In another embodiment of the invention, the lysine analog is tranexamic acid.

In another further embodiment of the invention, the precipitated biological mixture is provided frozen.

In another embodiment of the invention, the method further comprises the step of reducing the mean particle size of the frozen precipitated biological mixture to about 2-8 mm.

In one embodiment of the invention, the reduction in the mean particle size is carried out mechanically e.g. by a blender machine.

In another embodiment of the invention, the contacting step is carried out for more than 30 minutes e.g. 90 minutes.

In another embodiment of the invention, the separating step is carried out by centrifugation and/or filtration.

In one embodiment of the invention, the steps of partially dissolving the precipitated biological mixture and contacting the heterogeneous mixture with the immobilized inhibitor are carried out simultaneously.

In another embodiment of the invention, the partially dissolving conditions are selected from the group consisting of a pH range of 7.2-7.3, a temperature range of 30-32° C., an ethanol concentration in the range of 0.2 to 5%, and a combination thereof.

In another further embodiment of the invention, the partially dissolving conditions comprise a pH range of 7.2-7.3, a temperature range of 30-32° C., and an ethanol concentration in the range of 0.2 to 5%.

In another aspect, the invention relates to a method for purifying a macromolecule from a biological mixture comprising the macromolecule and a lytic enzyme specific to the macromolecule, the method comprising the steps of: providing the biological mixture as a heterogeneous mixture comprising the lytic enzyme, at least partially, in soluble form and the macromolecule, at least partially, in non-soluble form; providing an inhibitor of the lytic enzyme immobilized on a carrier; contacting the heterogeneous mixture with the immobilized inhibitor in batch form; increasing the solubility of the macromolecule in the mixture; and separating the immobilized inhibitor from the mixture.

Yet in another aspect, the invention relates to a macromolecule obtainable using the methods according to the invention.

DESCRIPTION OF EMBODIMENTS OF THE INVENTION

The present invention relates to an effective method for purifying a macromolecule of interest in its intact, non-degraded form from a mixture comprising said macromolecule in the presence of lytic enzymes.

"Intact macromolecule" and "non-degraded macromolecule" refers, for example, to the native, physiological, undamaged and/or functional macromolecule.

The present invention provides a method for removing a lytic enzyme from a biological mixture comprising the lytic enzyme and a macromolecule of interest that is sensitive to the lytic enzyme. The method comprises the following steps: providing the biological mixture as a heterogeneous mixture comprising the lytic enzyme in soluble form and the macromolecule in non-soluble form; providing an inhibitor of the lytic enzyme immobilized on a carrier; contacting the heterogeneous mixture with the immobilized inhibitor in batch form; increasing the solubility of the macromolecule in the mixture; and separating the immobilized inhibitor with the bound lytic enzyme from the mixture.

Without being bound by the mechanism it appears that contacting the heterogeneous mixture comprising the lytic enzyme with the immobilized inhibitor in batch form results in formation of an immobilized inhibitor-lytic enzyme complex.

The term "an immobilized inhibitor-lytic enzyme complex" refers to a composition comprising the immobilized inhibitor and the lytic enzyme associated by covalent or non-covalent bonds. The term "non covalent bonds" includes, but is not limited to, hydrogen bonds, ionic bonds, Van der Waals forces, hydrophobic or electrostatic interactions. The term "complex" also includes the plural form "complexes".

The present invention also provides a method for removing a lytic enzyme from a precipitated biological mixture comprising the lytic enzyme and a macromolecule of interest that is sensitive to the lytic enzyme, the method comprises the following steps: providing the precipitated biological mixture comprising the lytic enzyme and the macromolecule; providing an inhibitor of the lytic enzyme immobilized on a carrier; partially dissolving the precipitated biological mixture with an aqueous solution to obtain a heterogeneous mixture comprising solid particles; contacting the heterogeneous mixture with the immobilized inhibitor in batch form; dissolving the solid particles in the mixture; and separating the immobilized inhibitor with the bound lytic enzyme from the mixture.

The term "removing a lytic enzyme from a mixture" is used interchangeably with the term, "reducing the level of a lytic enzyme in the mixture", and refers to a decrease in the content of the lytic enzyme in the mixture.

The term "precipitated biological mixture" typically refers to a biological mixture comprising precipitates such as non-soluble and/or solid material.

The precipitated biological mixture can be provided e.g. by changing any parameter in a biological solution mixture that decreases the solubility of molecules in the solution such as temperature, pH, and concentration of organic solvents; and then the solid/non-soluble fraction can be separated and gathered e.g. by filtration, precipitation over time by the gravitation force and/or following centrifugation.

The term "partially dissolving the precipitated biological mixture" typically refers to not fully dissolving a precipitate with an aqueous solution leading to formation of a heterogeneous solution comprising solid and/or non-dissolved particles which are visible to the naked eye.

In one embodiment of the invention, the partial dissolving conditions comprise a pH level of 7.2-7.3. In another embodiment of the invention, the partial dissolving conditions comprise a temperature range of 30-32° C. In another further embodiment of the invention, the partial dissolving conditions comprise an ethanol concentration in the range of 0.2 to 5%. Yet, in another embodiment of the invention, the partial dissolving conditions comprise a pH level of 7.2-7.3, a temperature range of 30-32° C., and an ethanol concentration in the range of 0.2 to 5%. In one embodiment of the invention, the partial dissolving is carried out for a time period of less than 90 minutes (e.g. less than 85, 80, 75, 70, 65, 60, 55, 50, 45, 40, 35, 30, 25, 20, 15, 10, 5 minutes). It was found according to the present invention that suspending an aluminum hydroxide precipitated fraction and subjecting the precipitate to a solution comprising immobilized tranexamic acid (TEA) allowed removal of approximately 80% plasmin and/or plasminogen from the suspended precipitate. Thus, in one embodiment of the invention, about 80% (e.g. 80±20%) of the lytic enzyme is removed. "Macromolecule sensitive to a lytic enzyme" refers to a macromolecule that can be degraded and/or inactivated at least partially by the lytic enzyme. It was found according to the present invention that subjecting an aluminum hydroxide precipitate to immobilized TEA (an inhibitor of the proteolytic enzyme plasminogen/plasmin) at an early stage in the purification process of fibrinogen macromolecule (a macromolecule which is sensitive to and can be degraded by plasminogen/plasmin) resulted in a preparation with increased levels of functional fibrinogen as compared to a preparation obtained in the absence of the immobilized TEA. Also, it was surprisingly found according to the present invention that by adding the immobilized inhibitor (immobilized TEA) into a precipitate suspended under conditions that delayed solubilization of the macromolecule and/or augmented the solubilization of the lytic enzyme (forming a heterogeneous mixture), an efficient neutralization and fast removal of the lytic enzyme activity was obtained resulting in an optimal preparation with functional fibrinogen. More specifically, it was surprisingly found according to the present invention that the neutralization of the lytic enzyme occurred even though the precipitate has not been fully dissolved (i.e. is partially solubilized).

Without being bound by the mechanism, it appears that in the heterogeneous mixture the majority of the lytic enzyme is in soluble form and the majority of the macromolecule is in non-soluble form. In this way, the lytic enzyme (being in soluble form) is accessible and can be neutralized and/or captured by the immobilized inhibitor whereas the macromolecule (being in non-soluble form) is not accessible and presumably protected from lysis by the lytic enzyme. With time, gradual solubilization of the macromolecule occurs, the concentration and/or activity of the free lytic enzyme in the mixture decreases (since the majority of the lytic enzyme is inhibited and/or captured by the immobilized inhibitor), and therefore the solubilized macromolecule is protected from lysis by the lytic enzyme.

More particularly, it was found according to the present invention that using an immobilized inhibitor, instead of a soluble inhibitor, enabled to easily remove the majority of the lytic enzyme activity all together with the bulk of the immobilized inhibitor and other undesired process materials such as aluminum hydroxide e.g. by centrifugation and/or filtration.

In comparison, in the case that the soluble inhibitor is a small molecule (e.g. tranexamic acid of about 150 Daltons) its removal from the mixture, after use, is feasible only by carrying out multiple and exhaustive exclusion steps such as ultrafiltration and diafiltration.

In such an embodiment (using a small molecule as the inhibitor), due to difference of the molecular weight between the lytic enzyme and the soluble inhibitor (typically, the molecular weight of the lytic enzyme is about tens of Kilo Daltons and above and the molecular weight of the soluble inhibitors is typically less than 1 Kilo Dalton), the soluble inhibitor can be removed from the mixture by filtration while the lytic enzyme will remain in the mixture and its lytic activity will be undesirably restored.

Also, it was found according to the invention that contacting the lytic enzyme with the inhibitor by the batch method enables purification of intact macromolecules where the mixture comprising the macromolecule is heterogeneous and thus cannot be purified by a resin pre-packed in a column (referred to herein as "column purification") without adding preceding additional steps for obtaining a clear homogenous solution (e.g. solubilization of the particles, dialysis and/or filtration). Additionally, in a batch form the interaction surface and interaction speed between the enzyme and the inhibitor are greater as compared to column purification, expediting the neutralization process of the lytic enzyme.

"Column purification" generally refers to a technique in which a mixture is allowed to travel through a column comprising a packed resin at a certain flow rate, and an individual component is being adsorbed by the resin. Generally, column purification requires the removal of particulate material e.g. by centrifugation and/or filtration (to obtain a homogenous/clear solution) since conventional chromatography columns are quickly clogged by particles. The un-bound material is collected from the other side of the column after the mixture has passed through it. Column purification is well known in the art as described in Practical Protein Chromatography edited by Kenney and Fowell Volume 11 Humana Press, 1992.

As used herein, "batch method", "batch-wise", and "batch form" generally refer to a technique in which a mixture is contacted with a resin, typically in a single stage adsorption procedure. "A single stage adsorption procedure" refers to a procedure wherein all the components of the purification process (e.g. the resin and the mixture) are incubated together e.g. in a stirred tank, batch reactor or a vessel, and the adsorption is carried out in a continuous manner. The un-bound fraction can then be collected by an additional step of centrifugation and/or filtration.

In one embodiment of the invention, the mixture is contacted with the resin in a vessel e.g. a tube, and after an incubation period, the vessel is centrifuged and the supernatant comprising the macromolecule is collected. The batch method can be carried out in a vessel or a batch reactor.

The term "resin" refers to a "carrier" as defined below which typically comprises an immobilized inhibitor.

The findings according to the invention paved the way to the development of a method for rapidly and efficiently purifying a functional and/or intact macromolecule of interest from a heterogeneous biological mixture comprising a lytic enzyme and the macromolecule of interest by fast neutralization and removal of the lytic enzyme present in the mixture. In the heterogeneous mixture, the lytic enzyme is substantially in a soluble form whereas the macromolecule is substantially in a non-soluble form. The method comprises the following steps: providing a heterogeneous mixture comprising the lytic enzyme at least partially in soluble form and the macromolecule that is sensitive to the lytic enzyme at least partially in non-soluble form; providing an inhibitor of the lytic enzyme immobilized on a carrier; contacting the heterogeneous mixture with the immobilized inhibitor in batch form to allow the lytic enzyme to contact the immobilized inhibitor; increasing the solubility of the macromolecule in the mixture; and separating the immobilized inhibitor e.g. together with the bound lytic enzyme from the mixture.

"Fully soluble" means 100% dissolved e.g. without any solid particles. "Partially soluble" means less than 100% dissolved e.g. the lytic enzyme can be from about 5% to less than 100% dissolved. E.g. 5, 10, 15, 20, 25, 30, 35, 40, 45, 50, 55, 60, 65, 70, 75, 80, 85, 90, 95, 99 or less than 100%, including any range between the disclosed percentages such as 5-10%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 5-99%, 10-15%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 10-99%, 15-20%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 15-99%, 20-25%, 20-30%, 20-35%, 20-40%, 20-45%, 20-50%, 20-55%, 20-60%, 20-65%, 20-70%, 20-75%, 20-80%, 20-85%, 20-90%, 20-95%, 20-99%, 25-30%, 25-35%, 25-40%, 25-45%, 25-50%, 25-55%, 25-60%, 25-65%, 25-70%, 25-75%, 25-80%, 25-85%, 25-90%, 25-95%, 25-99%, 30-35%, 30-40%, 30-45%, 30-50%, 30-55%, 30-60%, 30-65%, 30-70%, 30-75%, 30-80%, 30-85%, 30-90%, 30-95%, 30-99%, 35-40%, 35-45%, 35-50%, 35-55%, 35-60%, 35-65%, 35-70%, 35-75%, 35-80%, 35-85%, 35-90%, 35-95%, 35-99%, 40-45%, 40-50%, 35-55%, 40-60%, 40-65%, 40-70%, 40-75%, 40-80%, 40-85%, 40-90%, 40-95%, 40-99%, 45-50%, 45-55%, 45-60%, 45-65%, 45-70%, 45-75%, 45-80%, 45-85%, 45-90%, 45-95%, 45-99%, 50-55%, 50-60%, 50-65%, 50-70%, 50-75%, 50-80%, 50-85%, 50-90%, 50-95%, 50-99%, 55-60%, 55-65%, 55-70%, 55-75%, 55-80%, 55-85%, 55-90%, 55-95%, 55-99%, 60-65%, 60-70%, 60-75%, 60-80%, 60-85%, 60-90%, 60-95%, 60-99%, 65-70%, 65-75%, 65-80%, 65-85%, 65-90%, 65-95%, 65-99%, 70-75%, 70-80%, 70-85%, 70-90%, 70-95%, 70-99%, 75-80%, 75-85%, 75-90%, 75-95%, 75-99%, 80-85%, 80-90%, 80-95%, 80-99%, 85-90%, 85-95%, 85-99%, 90-95%, 90-99%, 95-99%.

In one embodiment of the invention, the lytic enzyme is 50 to 95% dissolved. The percentages are from the total lytic enzyme present in the mixture.

"Fully non-soluble" means 100% in solid form e.g. frozen. "Partially non-soluble" means less than 100% in solid form e.g. the macromolecule can be about 5% to less than 100% in solid state E.g. 5, 10, 15, 20, 25, 30, 35, 40, 45, 50, 55, 60, 65, 70, 75, 80, 85, 90, 95, 99 or less than 100%, including any range between the disclosed percentages such as 5-10%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 5-99%, 10-15%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 10-99%, 15-20%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 15-99%, 20-25%, 20-30%, 20-35%, 20-40%, 20-45%, 20-50%, 20-55%, 20-60%, 20-65%, 20-70%, 20-75%, 20-80%, 20-85%, 20-90%, 20-95%, 20-99%, 25-30%, 25-35%, 25-40%, 25-45%, 25-50%, 25-55%, 25-60%, 25-65%, 25-70%, 25-75%, 25-80%, 25-85%, 25-90%, 25-95%, 25-99%, 30-35%, 30-40%, 30-45%, 30-50%, 30-55%, 30-60%, 30-65%, 30-70%, 30-75%, 30-80%, 30-85%, 30-90%, 30-95%, 30-99%, 35-40%, 35-45%, 35-50%, 35-55%, 35-60%, 35-65%, 35-70%, 35-75%, 35-80%, 35-85%, 35-90%, 35-95%, 35-99%, 40-45%, 40-50%, 35-55%, 40-60%, 40-65%, 40-70%, 40-75%, 40-80%, 40-85%, 40-90%, 40-95%, 40-99%, 45-50%, 45-55%, 45-60%, 45-65%, 45-70%, 45-75%, 45-80%, 45-85%, 45-90%, 45-95%, 45-99%, 50-55%, 50-60%, 50-65%, 50-70%, 50-75%, 50-80%, 50-85%, 50-90%, 50-95%, 50-99%, 55-60%, 55-65%, 55-70%, 55-75%, 55-80%, 55-85%, 55-90%, 55-95%, 55-99%, 60-65%, 60-70%, 60-75%, 60-80%, 60-85%, 60-90%, 60-95%, 60-99%, 65-70%, 65-75%, 65-80%, 65-85%, 65-90%, 65-95%, 65-99%, 70-75%, 70-80%, 70-85%, 70-90%, 70-95%, 70-99%, 75-80%, 75-85%, 75-90%, 75-95%, 75-99%, 80-85%, 80-90%, 80-95%, 80-99%, 85-90%, 85-95%, 85-99%, 90-95%, 90-99%, 95-99%. In one embodiment of the invention, the macromolecule is 50 to 95% in solid form. The percentages are from the total macromolecule present in the mixture.

A biological mixture can comprise a cell fraction such as platelet extract; an animal tissue extract; an animal bone extract; a gelatin or collagen enriched mixture from animal source; mixtures comprising bovine serum albumin; an animal derived water immiscible fat; a cell culture extract; or a cell culture exudate such as recombinant proteins or bacterial extract fractions such as inclusion bodies.

The term "platelet extract" refers to a mixture comprising platelet-derived factors. Typically, extracts are cell free.

The term "animal" as used herein includes mammalian and human subjects.

The biological mixture can be derived from mammalian and human body fluids. In one embodiment, the biological mixture is semen, sputum, urine, feces, sweat, saliva, nasal mucus, cerebrospinal fluid, and a blood fraction i.e. a product of whole blood such as cryoprecipitate, plasma, or serum. The biological mixture can be a protein precipitate.

The biological mixture can be a precipitated fraction from human plasma, a precipitated fraction from a suspended cryoprecipitate or a precipitated fraction from human plasma.

The precipitate can be a cryoprecipitate. The term "cryoprecipitate" refers to a blood component which is obtained from frozen plasma prepared from whole blood, recovered plasma or from source plasma which is collected by plasmapheresis. A cryoprecipitate can be obtained when frozen plasma is slowly thawed in the cold, typically at a temperature of 0-4° C., resulting in the formation of a precipitate that contains fibrinogen and factor XIII. The precipitate can be collected, for example by centrifugation.

The precipitate can be a by-product from the manufacture process of FVIII e.g. acid-precipitate, chill-precipitate, aluminum hydroxide precipitate (see, for example, U.S. Pat. No. 4,455,300), glycine precipitate (see, for example, U.S. Pat. No. 4,297,344), ethanol precipitate and heparin precipitated paste.

The term "by-product" refers to an undesired and/or unintended and/or non used material and/or residual material usually produced or formed in the course of an industrial or biological process in addition to the desired material/product.

The term "precipitate" and "precipitated fraction" are interchangeable.

In one embodiment of the invention, the protein precipitate is an aluminum hydroxide precipitate. Advantageously, when a precipitate comprises aluminum hydroxide, the aluminum hydroxide can be easily removed from the suspended precipitate together with the vitamin-K depended proteases e.g. by centrifugation and/or filtration. In contrast, when a precipitate comprises heparin, the heparin cannot be easily removed from the suspended precipitate by centrifugation and/or filtration since the heparin solubilizes in the aqueous solution. Even if the heparin may be removed by a more complex process, e.g. ultrafiltration, un-inhibited lytic enzymes e.g. proteases will be left behind in the solution free to attack the macromolecule of interest.

As used herein, the term "lytic enzyme" refers to an enzyme capable of specifically or non-specifically degrading substrate molecules. The term lytic enzyme includes, but is not limited to, enzymes that degrade proteins (i.e. proteases such as collagenase, plasmin, and/or plasminogen), fats (i.e. lipases), DNA (i.e. DNAases), RNA (i.e. RNAases), starch (i.e. amylase), and cellulose (i.e. cellulase). In one embodiment of the invention, the size of the lytic enzyme is in the range of about tens of Kilo Daltons and above.

The term "a macromolecule of interest" typically refers to any macromolecule present in a mixture for which purification is desired, and includes any bio-polymer such as proteins, lipids, nucleic acids, carbohydrates e.g. glycogen and cellulose. Typically, protein macromolecules have a molecular weight from tens to million Kilo Daltons. In one embodiment of the invention, the size of the macromolecule is in the range of about hundreds of Kilo Daltons and above.

The term "a lytic enzyme" may refer to a single or a mixture of lytic enzymes and the term "a macromolecule" may refer to a single or a combination of macromolecules. In one embodiment of the invention, the macromolecule is a protein and the lytic enzyme is a protease (i.e. a proteolytic enzyme). In another embodiment, the protein is fibrinogen (molecular weight of about 270,000-340,000 Daltons). In a further embodiment of the invention the proteolytic enzyme is plasmin and/or its zymogen plasminogen [called herein "plasmin(ogen)", MW of about 75,000-90,000 Daltons].

In another further embodiment of the invention, the macromolecule in the biological mixture is water immiscible fats and the lytic enzyme is a lipase. In such an embodiment, in order to obtain a heterogeneous mixture, the biological mixture can be kept at low temperatures and above freezing temperature. In such conditions, the lipase is dissolved in the water accessible to its inhibitor whereas the water immiscible fats are in non-soluble form and inaccessible to degradation by the lipase. The term "heterogeneous mixture" refers herein to a mixture which comprises solids, is partially dissolved and/or not fully solubilized and cannot be passed through and subjected to column purification (e.g. affinity chromatography, gel filtration, ion exchanger, hydrophobic interaction) without adding preceding additional steps of clearing or homogenization e.g. solubilization of the particles, dialysis, filtration and/or the like.

Adding preceding steps for removing the particles from the mixture can be time-consuming and expensive and can also undesirably remove the macromolecule of interest which is present in the mixture in a non-soluble solid form, consequently resulting in a low yield of the purified macromolecule. Advantageously, the method of the invention is carried out without removing the solid particles from the mixture consequently resulting in an increased yield of the purified macromolecule. In one embodiment of the invention, the yield of the macromolecule is at least 90%.

A heterogeneous mixture generally refers to a mixture that comprises a liquid and particles e.g. non-soluble and/or solid particles. In one embodiment, the heterogeneous mixture is composed of about 50 to 95% (w/w) liquid phase. In another embodiment, the heterogeneous mixture is composed of about 5 to 50% (w/w) non-soluble and/or solid particles. In a further embodiment, the heterogeneous mixture is composed of 80% (w/w) liquid phase and 20% (w/w) non-soluble and/or solid particles. The above percentages refer to the fraction of the liquid and the particles in the mixture at the beginning of carrying out the method. However, with time the particles may dissolve and the ratio by weight of non-soluble and/or solid particles to liquid phase can consequently be altered.

In one embodiment of the invention, the heterogeneous mixture comprises precipitated particles suspended in an aqueous solution.

The heterogeneous mixture comprises the majority of the lytic enzyme in soluble form and the majority of the macromolecule in non-soluble form.

It was found according to the present invention that a heterogeneous mixture can be obtained from a precipitate by suspending the precipitate with an aqueous solution under conditions that slows down the solubilization rate of the macromolecule and/or augment the solubilization rate of the lytic enzyme. These conditions were achieved e.g. by adjustment of the pH level to 7.2-7.3, the temperature to 30-32° C., and by decreasing the ethanol concentration from about 5% to about 1%.

Accordingly, a heterogeneous mixture can be provided by starting with solid particles comprising the lytic enzyme and the macromolecule (e.g. a pellet), and suspending the solid particles with an aqueous solution under conditions that delay the solubilization of the macromolecule into the mixture. Alternatively or in parallel, the solubility of the lytic enzyme can be manipulated e.g. by the addition of agents leading to salting in of the enzyme such as addition of sodium chloride or chaotropic agents such as urea or guanidine hydrochloride.

The term "pellet" refers to the non-soluble and/or solid fraction of the solution that is separated from the solution due to a change in any parameter that decreases the solubility of molecules in the solution such as temperature, pH, and concentration of organic solvents; and/or refers to an aggregate of protein molecules large enough to be visible to the naked eye and which can be collected by centrifugation at about 10,000 g. The non-soluble, solid fraction and/or the aggregate protein molecules can be gathered e.g. by filtration, precipitation over time by the gravitation force and/or following centrifugation.

The term "pellet" is oftentimes interchangeable with the term "precipitate". The non soluble and/or solid particles can be provided into the method of the invention in a frozen state. A "frozen state" can be obtained at a temperature at which a liquid of a specified composition solidifies under a specified pressure. The term "frozen state" is used herein to include a semi or fully frozen state.

In one embodiment of the invention, the conditions that delay solubilization of the macromolecule and/or augment the solubilization of the lytic enzyme comprise a pH level in the range of 7.2-7.3. In another embodiment of the invention, the conditions comprise a temperature range of 30-32° C. Yet, in another embodiment of the invention, the conditions comprise an ethanol concentration in the range of 0.2 to 5%. Yet, in another further embodiment of the invention, the conditions comprise a pH level in the range of 7.2-7.3, a temperature range of 30-32° C., and an ethanol concentration in the range of 0.2 to 5%.

Alternatively, a heterogeneous mixture can be provided by starting with a homogenous mixture comprising the enzyme and the macromolecule and selectively decreasing the solubility of the macromolecule in the mixture.

The decrease in the solubility of the macromolecule in the mixture can be achieved e.g. by cooling, pH adjustment, addition of solvents such as acetone and ethanol, addition of agents such as polyethylene glycol (PEG) and polyvalent substances, addition of anti-chaotropic salts such as ammonium sulfate and sodium sulfate, addition of salts or other agents causing salting out such as sodium chloride and/or the like.

In one embodiment of the invention, the macromolecule is fibrinogen, the lytic enzyme is plasmin and/or plasminogen, and the inhibitor is a lysine analog such as tranexamic acid and 4-aminomethylbicyclo-[2.2.2.]-octane-1-carboxylic acid (EMBOCA).

In another embodiment of the invention, the biological mixture is a protein precipitate e.g. an ethanol containing protein precipitate. In another further embodiment of the invention, a heterogeneous mixture is provided by suspending the ethanol containing (e.g. in the concentration of up to 10% ethanol) protein precipitate comprising fibrinogen and plasmin(ogen) with a solvent. In another embodiment of the invention, the suspension is carried out at a low temperature (e.g. in the range of −4 to 20° C.). In another embodiment of the invention, the suspension is carried out in an ethanol concentration in the range of 0.2 to 5%, at a low pH value (e.g. lower than 7.3), and at a temperature of 30-32° C. In one embodiment of the invention, under these conditions, solubilization of the fibrinogen macromolecule is selectively delayed and solubilization of plasmin(ogen) is augmented. In one embodiment of the invention, the solvent is an aqueous solution. The aqueous solution can comprise sodium chloride, tri-sodium citrate dehydrate, human serum albumin, tri-sodium citrate, glycine, alhydrogel [Al(OH)$_3$]. The addition of the immobilized inhibitor to the mixture can be carried out at the suspension step by supplementing the aqueous solution used for suspending the precipitate with the immobilized inhibitor. The aqueous solution used for suspending the protein precipitate can be pre-heated (e.g. to a temperature of 34° C.) prior to use. The suspension buffer can be added into the precipitate at a ratio of 1:4 between the weight of the precipitate and the volume of the suspension buffer, respectively.

As used herein the term "an inhibitor immobilized on a carrier" refers to any mode of association of the inhibitor with a surface of the carrier material. The inhibitor can be attached to the carrier by covalent bonding, ionic bonding, physical bonding, cross-linking with a bi-functional reagent and/or by any other method known to those skilled in the art.

The carrier can have a hydrophobic or a hydrophilic surface that interacts with at least a part of the inhibitor by hydrophobic/hydrophilic covalent interaction. The hydrophobic/hydrophilic surface of the carrier may also be a polymer such as plastic or any other polymer wherein hydrophobic/hydrophilic groups have been linked to such as polyethylene, polystyrene or polyvinyl. Alternatively, the inhibitor can be covalently bound to the carrier via a molecule or a linker bridging between the carrier and the inhibitor. The term "linker" as used above refers to a spacer arm or a leash having a molecular weight from tens to million Daltons that is used as an intermediary connector between the carrier and the inhibitor. E.g. the linker can be a protein, a peptide and/or an amino acid. In case the carrier binds directly the inhibitor (without a linker), a reactive group within the inhibitor, such as a hydroxyl group, an ester or an amino group or carboxy group may be used to join to a reactive group present on the carrier in order to create the covalent bond. The carrier may also have a charged surface or can be modified to carry a charged group that interacts with the inhibitor. The carrier may have other reactive groups that can be chemically activated so as to attach the inhibitor. For example, cyanogen bromide activated matrices, epoxy activated matrices, N-hydroxy succinimide activated matrices, di-arachidonyl phosphatidic acid (DAPA) activated matrices, diaminodipropylamine (DADPA) activated matrices, 1,6diaminohexane activated matrices, succinic acid activated matrices, 1,3diamino-2-propanol activated matrices, ethylendiamine (EDA) activated matrices, 5-thio-2-nitrobenzoic acid activated matrices, pyridyldisulfide activated matrices, iodoacetamide activated matrices, maleimide activated matrices or combinations thereof. The carrier may also comprise an inorganic material such as silicon oxide material, e.g. silica gel, to which the inhibitor can be covalently linked. The term "carrier" as used herein includes a support, or any material used to attach, immobilize, carry, or stabilize the inhibitor. Supports are well known in the art as described in Hermanson et al. Immobilized Affinity Ligand Techniques (Academic Press Inc. 1992). The support for carrying out the method of the invention can be any material which is capable of binding the inhibitor.

In one embodiment of the invention the support/carrier is a chromatographic material. The chromatographic material can be a hydrophilic material such as agarose, sepharose, acrylic beads, cellulose, controlled pore glass, silica gels, dextranes; hydrophobic material such as resin; or an organic artificial/synthetic polymer such as materials based on poly-acrylamides polystyrens. Typical materials/polymers are commercially available under the trade names Sephacryl® (Pharmacia, Sweden), Ultragel® (Biosepara, France), TSK-Gel Toyopearl® (Toso Corp., Japan), HEMA (Alltech Ass. (Deer-field, Ill., USA), Eupergit® (Rohm Pharma, Darmstadt, Germany). Also materials based on azlactones (3M, St. Paul, Minn., USA). Particularly preferred is Agarose® or Sepharose®. These materials are commercially available, for example, from Sigma, St. Louis. In one embodiment of the invention, the carrier is a FRACTOGEL® EMD, a TOYOPEARL®, or a TSK-GEL® polymer matrix.

The carrier materials can be solid or fluid. Solid supports include, but are not limited to, matrices, microchip (for example, silicon, silicon-glass, or gold chip), coverslips, chromatographic materials, microscope slides, test tubes, vials, bottles, microtiter dish, ELISA supports, glass or plastic surfaces, sheets, particles (for example, agarose or sepharose), beads including magnetic beads, gels, powders, fibers, and the like. In one embodiment of the invention, the carrier is a chromatographic material which is suspended in an appropriate medium and the resulting slurry is used in batch chromatography method e.g. by using a test tube, vial, bottle, batch reactor and the like.

The term "inhibitor of the lytic enzyme" refers to any agent (including an antagonist) that is capable of binding (or capturing) the lytic enzyme and directly or indirectly interferes with its lytic activity against the macromolecule of interest. The inhibitor can bind to the catalytic site, substrate binding site, allosteric site or any other part of the lytic enzyme. A competitive inhibitor which competes with the binding of the macromolecule to the lytic enzyme can be used. The binding of the inhibitor to the lytic enzyme may be reversible or irreversible. The inhibitors can be of natural origin, synthetic origin or natural origin with synthetic modifications.

The inhibitor can be a small molecule (e.g. an amino acid such as lysine or an amino acid analog such as tranexamic acid and EMBOCA), a polypeptide such as a specific antibody or fragments thereof as long as they exhibit the binding specificity as the entire antibody, a ribonuclease inhibitor, a short peptide or peptidomimetic sequence. In one embodiment of the invention, the inhibitor is an amino acid analog such as a lysine analog. In another embodiment of the invention, the lysine analog is tranexamic acid.

The term "contacting" refers to a combining action which brings the heterogeneous mixture into contact with the carrier and more particularly to a combining action which brings the lytic enzyme into contact with the immobilized inhibitor in a manner that a binding interaction will occur between the inhibitor and the lytic enzyme present in the mixture. The mixture can be incubated with the carrier for a sufficient period of time which allows contacting, binding and/or complexing between the immobilized inhibitor and the lytic enzyme.

It was found according to the present invention that contacting the heterogeneous mixture with the carrier comprising the immobilized inhibitor for an incubation period of 90 minutes resulted in a preparation with increased levels of functional fibrinogen as compared a preparation obtained following a shorter incubation period of 30 minutes. Thus, the mixture can be contacted with the carrier comprising the immobilized inhibitor for an incubation period of more than 30 minutes e.g. 35, 40, 45, 50, 55, 60, 65, 70, 75, 80, 85, and 90 minutes or more.

Without being bound by the mechanism, it appears that a prolonged incubation enables capture and subsequently removal of the majority of the proteolytic enzyme thereby obtaining a stable, non-degraded, and functional fibrinogen macromolecule.

It was also found according to the present invention that when the starting material is provided into the method of the invention in a solid form e.g. in a frozen form, reducing the mean particle size of the solid prior to contacting the mixture with the immobilized inhibitor resulted in a preparation with increased levels of functional fibrinogen.

Without being bound by the mechanism, it appears that reducing the mean particle size of the solid maximizes the contact surface area of the solid to the carrier comprising the immobilized inhibitor during the contacting step resulting in a quick and efficient binding and neutralization of the lytic enzyme.

The mean particle size of the solid can be reduced mechanically e.g. by using a blender machine, rotary blades or bladed sieves; manually e.g. by using scissors or by shattering the solid with a hammer and/or a chisel; or by any other method known in the art.

It was surprisingly found according to the present invention that reducing the mean particle size of a frozen pellet with a chisel and a hammer (to obtain particles smaller than 5 cm), followed by a mechanical grinding (to obtain particles of 2-8 mm) resulted in better recovery of functional fibrinogen as compared to reducing the mean particle size with a chisel and a hammer, followed by a manual grinding (i.e. cutting the pellet with scissors).

Typically, mechanical grinding is faster, produces uniform sized particles, and can be initiated at a lower temperature (as compared to the manual grinding)—minimizing the beginning of the lytic process, but on the other hand during the procedure itself heat may be produced and applied to the material and therefore harm the protein activity. In contrast, manual grinding (e.g. by using scissors) is gentle, but is time consuming and may lead to production of variable sized particles. As indicated, optimal fibrinogen function and recovery was observed using the mechanical grinding method.

The term "mechanical grinding method" refers to shearing methods employing use of a machine utilizing an energy source such as electricity or hydraulic energy. A "manual grinding method" typically refers to shearing methods based on the operator's physical force e.g. cutting the solid particles with scissors.

In one embodiment of the invention, the mean particle size of the solid (e.g. precipitate) is reduced to about 2-8 mm prior to contacting the heterogeneous mixture with the immobilized inhibitor. In another embodiment of the invention, the reduction in the mean particle size of the solid is carried out mechanically.

In another further embodiment of the invention, the reduction in the mean particle size of the solid is carried out by a blender machine. In another embodiment of the invention, prior to the mechanical grinding, the solid material (e.g. a frozen precipitate) is shattered/broken with a chisel and hammer e.g. to obtain a mean particle size of <5 cm.

It was found according to the invention, that once the lytic enzyme is captured and neutralized in the complex with the immobilized inhibitor, the macromolecule is protected and can be "safely" solubilized.

Accordingly, following contacting the heterogeneous mixture with the carrier comprising the immobilized inhibitor in batch form, the solubility of the macromolecule is increased.

In a subsequent step, the immobilized inhibitor complexed with the lytic enzyme is separated from the mixture.

Increasing the solubility of the macromolecule and/or dissolving the solid particles in the mixture can be carried out by altering the conditions of the mixture as elaborated above and/or the solubility of the macromolecule can be accomplished following a prolonged incubation time.

Separation of the immobilized inhibitor with the bound lytic enzyme from the mixture can be carried out by centrifugation and/or filtration. The centrifugation can be non-continuous (e.g. at 17,000 g for 25 minutes at room temperature) or continuous.

Continuous centrifugation is generally used for processing industrial volumes of liquid. It is carried out by continuously feeding a fluid into a rotor, collecting the sediment in the rotor while withdrawing the supernatant continuously as the rotor rotates. Non-continuous centrifugation generally refers to a centrifugation process in which the liquid is fed in defined portions per each centrifugation cycle ("batch") and the supernatant is withdrawn at the end of the centrifugation cycle after a full stop of the centrifuge.

Generally, following the centrifugation step, the supernatant is collected leaving an undesired pellet of the bulk of the immobilized inhibitor and the captured lytic enzyme.

In case that aluminum hydroxide precipitate is used as the starting material, centrifugation advantageously achieves removal of both: the bulk of the aluminum hydroxide and the complexed lytic enzyme-immobilized inhibitor all in one step. A successive filtration step (e.g. through 3 and 1-1.2 µm filters) can be carried out in order to remove residual amounts of the immobilized inhibitor and the captured lytic enzyme.

In case that magnetic beads are used as the carrier, separation can be carried out by magnetic bead-based separation technology e.g. as described in Bjørn-Ivor Haukanes & Catrine Kvam. Application of Magnetic Beads in Bioassays. Nature Biotechnology 11, 60-63 (1993).

The immobilized inhibitor can be reconstituted and reused, e.g. by releasing the bound lytic enzyme using a high salt concentration or by using a high concentration of the solubilized form of the inhibitor and then separating between the released lytic enzyme and the immobilized inhibitor (e.g. by centrifugation).

Biological materials derived from blood components are typically purified from infective particles in order to minimize the potential risk posed by blood-borne pathogens.

The purification procedure can be carried out by nanofiltration, solvent/detergent treatment, heat treatment, gamma or UVC (<280 nm) irradiation, or by any other method known in the art.

The term "infective particle" refers to a microscopic particle, such as, but not limited to, a microorganism or a prion, which can infect or propagate in a biological organism. The infective particles can be viral particles.

The inactivation procedure of infective particles can be carried out by adding a molecule to the mixture prior to and/or during the procedure. The added molecules and their products can be removed by gravitation, column chromatography phase separation or by any other method known in the art. The removal of infective particles can be carried out by filtration or by selective absorption methods such as affinity, ion exchange or hydrophobic chromatography. A multi-step viral inactivation procedure can be carried out. For example, the mixture can be subjected to solvent/detergent treatment, pasteurization, selective chromatography and nanofiltration.

The term "viral inactivation" refers both to the situation wherein viruses are maintained in the mixture but are rendered non-viable (for example, by dissolving their lipid coat), and/or to the situation wherein viruses are physically removal from the mixture (for example, by size exclusion techniques).

"Solvent detergent (S/D) treatment" typically refers to a process that inactivates enveloped or lipid-coated viruses by destroying their lipid envelope. The treatment can be carried out by the addition of detergents (such as Triton X-45, Triton X-100 or Tween 80) and solvents [such as tri(n-butyl) phosphate (TnBP), di- or trialkylphosphates]. The solvent-detergent combination used to deactivate lipid coated viruses may be any solvent-detergent combination known in the art such as TnBP and Triton X-100; Tween 80 and Sodium cholate and other combinations.

The concentration of the solvent(s) and detergent(s) used can be those commonly used in the art, for example, >0.1% TnBP and >0.1% Triton X-100. In another embodiment of the invention a combination of 1% Triton X-100 and 0.3% TnBP is used. Typically, the conditions under which the solvent-detergent inactivates the viruses consist of 10-100 mg/ml of solvent-detergent at a pH level ranging from 5-8, and a temperature ranging from 2-37° C. for 30 min. to 24 hours. However, other solvent-detergent combinations and suitable conditions will be apparent to any person versed in the art. The bulk of the solvent-detergent used in the S/D treatment can be removed, for example, by using chromatography columns such as hydrophobic interaction chromatography column (HIC) e.g. C-18 silica packing material and SDR (Solvent-Detergent removal) HyperD; protein adsorption matrices such as ion-exchange matrices; affinity matrices; oil extraction and/or size-exclusion matrices. In one embodiment of the invention, SDR HyperD, which is a chromatographic packing made of silica beads in which the pore volume is filled with a three-dimensional cross-linked hydrophobic acrylic polymer, is used to remove the solvent-detergent. The SDR HyperD advantageously involves a mixed-mode adsorption of hydrophobic interaction and is associated with a molecular exclusion effect [Guerrier L et al. "Specific sorbent to remove solvent-detergent mixtures from virus-inactivated biological fluids". J Chromatogr B Biomed Appl. 1995 Feb. 3; 664(1):119-125].

"Pasteurization" typically refers to a process by which heat destroys both lipid-enveloped and non-enveloped viruses. "Pasteurization" is interchangeable with the term "heat inactivation" or "heat treatment". The heat inactivation can be carried out at about 60° C. for about 10 hours. Stabilizers such as sucrose and glycine can be added into the mixture during the pasteurization step.

"Nanofiltration" typically refers to a process by which lipid-enveloped and non-enveloped viruses are excluded from the mixture e.g. by using nanometer-scale filters such as Planova™ 20N, 35N and 75N; Viresolve/70™, Viresolve/18™.

The filters can have a pore size of less than 70 nm, preferably between 15 and 50 nm. However, any membrane having a pore size sufficient to reduce or eliminate viruses from the sample can be employed in nanofiltration. Viruses removed by nanofiltration can be enveloped [e.g. HIV, hepatitis B virus, hepatitis C virus, West Nile Virus, cytomegalovirus (CMV), Epstein-Barr virus (EBV), herpes simplex virus], and non enveloped (e.g. hepatitis A virus, paravirus B19, Polio virus).

The mixture can be concentrated by ultra-filtration process. The ultrafiltration can be followed by diafiltration to exchange the buffer. The concentration and dialysis by ultrafiltration and diafiltration, respectively, can be carried out in one step or as two separate steps. The diafiltration can be carried out against any solution which is suitable for human administration.

At a later step of the purification, the mixture is homogenous and, if desired, it can be passed through and subjected to column purification for further purification of residual lytic enzyme e.g. by using an affinity column packed with the immobilized inhibitor. In the case that the lytic enzyme is plasmin(ogen), the macromolecule of interest is fibrinogen, and the inhibitor is TEA and/or EMBOCA, a chromatographic method as described in U.S. Pat. No. 7,125,569 and WO02095019 can be used.

Often, starting materials for macromolecule purification are pellets or precipitates such as aluminum hydroxide precipitate, ethanol precipitate, acid-precipitate, chill-precipitate, glycine precipitate and heparin precipitated paste, which comprise the macromolecule of interest. However, besides the macromolecule of interest, these materials comprise a great deal of lytic enzymes to which those macromolecules are sensitive. Typically, prior to removal of these lytic enzymes (e.g. by column chromatography purification) the material is subjected to a step of full solubilization to obtain a homogenous solution capable of running through the column. However, during or after the full solubilization, the macromolecule becomes accessible to degradation by the lytic enzymes to some extent.

Advantageously, in the method provided by the present invention, lytic enzymes are captured and neutralized early in the purification or manufacture process when the macromolecule is in non-soluble form or before the starting material is fully solubilized. For example, an immobilized inhibitor of the lytic enzyme is added to the heterogeneous mixture comprising the soluble lytic enzyme and the insoluble macromolecule. Also, using in the method an immobilized inhibitor in batch form before the starting material is fully solubilized enables fast neutralization of the lytic enzyme at the beginning of the macromolecule purification process. The next step of full solubilization of the macromolecule and separation (e.g. centrifugation) allows the removal of the majority of lytic enzyme all together with the bulk of inhibitor, and allows obtaining a preparation with the macromolecule of interest in its intact, non-degraded form.

In one embodiment of the invention, the lytic enzyme plasmin and/or plasminogen is removed from a frozen aluminum hydroxide precipitate which comprises the lytic enzyme and a fibrinogen macromolecule. In such an embodiment, the inhibitor can be tranexamic acid (TEA) which is immobilized on sepharose gel. The components required for the purification process are added in batch form before the precipitate is fully solubilized or fully dissolved. In another embodiment of the invention, the purification procedure is carried out as follows: a frozen aluminum hydroxide precipitate (pellet) is obtained; the frozen precipitate is shattered with a hammer and a chisel until particles of <5 cm are obtained; the shattered particles are incubated at 4° C. for approximately 1 hour (until the pellet material reaches a temperature of about 0° C.); the particles are sheared using a blender machine by 2-3 pulses of 15-20 sec. each with 40 sec. intervals between pulses, until particles of a few mm are obtained e.g. 2-8 mm; the blended particles are mixed with a pre-heated (34° C.) suspension buffer at a ratio of 1:4 between the weight of the ice pieces and the volume of the suspension buffer (e.g. 7 g NaCl; 2.95 g tri-sodium citrate dehydrate; 8 mg/ml Human Serum Albumin; and pure water to 1 Liter; pH=7.4; 6-40 ml settled TEA-Sepharose; and Optionally 3.6 g of 2% Al(OH)$_3$; at pH 7.4); the obtained mixture is stirred for 90 minutes while maintaining a temperature of 30-32° C. and a pH level of 7.2; the mixture is centrifuged e.g. in a non-continuous manner (17,000 g; 25 min; room temperature) or in a continuous manner; the obtained supernatant is filtered through a 3 µm filter e.g. polypropylene filter followed by a 1-1.2 µm filter e.g. glass fiber plus filter; stabilizers are added (e.g. Ca$^{2+}$ and glycine); double viral inactivation steps are carried out e.g. solvent/detergent (S/D) treatment followed by pasteurization; an ultrafiltration/diafiltration step is carried out; the obtained solution is subjected to column purification using TEA-Sepharose column e.g. as disclosed in U.S. Pat. No. 7,125,569 and WO02095019; and a composition enriched with fibrinogen is obtained.

Thus, the invention also enables obtaining a preparation enriched with the macromolecule of interest in its intact, non-degraded form and/or a purified preparation of the macromolecule in its intact, non-degraded form.

In one embodiment of the invention, the macromolecule of interest is fibrinogen and the term "a preparation enriched with fibrinogen" refers to a preparation which comprises at least 10 mg/ml (e.g. 15, 20, 25, 30, 35, 40, 45, 50, 55, 60, 65 mg/ml or more) functional fibrinogen.

The term "purified preparation of the macromolecule", as used herein, refers to a preparation obtained following removal of at least 80% (e.g. 80±20%) of the lytic enzyme from the starting material (e.g. a biological mixture and/or a precipitated biological mixture) comprising the lytic enzyme and the macromolecule.

Concentration of functional fibrinogen can be measured by the modified, European Pharmacopeia Assay (0903/1997) procedure as elaborated in: European Pharmacopaiea, Fibrin sealant kit. 1997; 0903:858; and Clauss A. Gerinnungsphysiologische Schnellmethode zur Bestimmung des Fibrinogens. Acta Haematol. 1957; 17: 237-246; or by any other method known in the art.

The disclosure of applications, patents and publications, cited above or below, is hereby incorporated by reference.

The invention is based on the following experiments and findings which exemplify the method according to the invention. The following examples are illustrative but not limiting.

EXAMPLES

In the following experiments the proteolytic enzyme plasmin and/or plasminogen [called herein "plasmin(ogen)"] was removed from a frozen aluminum hydroxide precipitate which comprised the fibrinogen macromolecule and the proteolytic enzyme plasmin(ogen).

Materials and Methods.

Aluminum Hydroxide Precipitate Preparation.

Aluminum hydroxide precipitate (called herein "pellet") is a byproduct obtained during the manufacturing process of Factor VIII (FVIII).

Generally, during preparation of FVIII, fibrinogen, fibronectin, factor XIII together with proteases such as plasmin(ogen) are precipitated from a re-suspended cryoprecipitate by the addition of ethanol at low temperature followed by a step of centrifugation. Prior to the centrifugation step, aluminum hydroxide is added to the re-suspended cryoprecipitate resulting in the precipitation of vitamin K-dependent coagulation factors such as factor II, VII and X with the aluminum hydroxide during the centrifugation step. The obtained aluminum hydroxide precipitate containing fibrinogen, fibronectin, and factor XIII was then separated from the FVIII containing supernatant and used in the experiments described below.

In more detail, the aluminum hydroxide precipitate was obtained by carrying out the following steps: A cryoprecipitate was prepared essentially as described in WO 93/05822 and WO 94/22503. Briefly, the cryoprecipitate was prepared from frozen (−30° C.) human plasma which was thawed at 4° C. and the supernatant was removed. The cryoprecipitate was frozen to −30° C. followed by thawing at 0-4° C. In the next step, the thawed cryoprecipitate was re-suspended at 10° to 20° C. in a double volume of WFI (water for injection) containing 1 to 3 U/ml heparin sodium (heparin was added as a protease inhibitor). The pH was adjusted to a level of 7-8 using diluted acetic acid. Then, 5% ethanol (to promote fibrinogen precipitation) containing 1 to 3 U/ml heparin sodium was added into the mixture in the same volume of the mixture (w/v) at a temperature of 10 to 20° C. The pH was adjusted to 6.8-7.2 using diluted acetic acid. The mixture was cooled to a temperature of 10°-15° C. while stirring and aluminum hydroxide (added to precipitate the vitamin K dependent coagulation factors) was added into the re-suspended cryoprecipitate to a final concentration of approximately 0.05%. This step was followed by a centrifugation step (carried out at 17,000 g for 25 min at 14-18° C.). The supernatant (containing FVIII) was removed and the pellet was obtained. This pellet contained inter alia fibrinogen, factor XIII, fibronectin, proteolytic enzymes such as plasmin (ogen), aluminum hydroxide and vitamin K dependent coagulation factors. The pellet comprised a high concentration of ethanol (~5% ethanol) and had a pH level of lower than 7.2. The pellet material was frozen and kept at −80° C. until further processing.

Fibrinogen Concentration.

Fibrinogen concentration was measured by the Clauss clotting time method. This method measures functional fibrinogen levels in an unknown sample according to its clotting time in the presence of a constant amount of thrombin using a clotting time machine. The clotting time measured for the unknown sample is compared to those obtained with a calibration curve produced with a fibrinogen standard. The method used is a modification of the Eu. Ph. assay 0903/1997 as elaborated in: European Pharmacopaiea, Fibrin sealant kit. 1997; 0903: 858; and Clauss A. Gerinnungsphysiologische Schnellmethode zur Bestimmung des Fibrinogens. Acta Haematol. 1957; 17: 237-246.

Solvent/Detergent (S/D) Treatment.

1% (w/w) of each of TnBP (Tri-n-butylphosphate) and Triton X-100 (S/D mixture) were added into the composition (pre-warmed to 30° C.) while mixing (approx. 150 rpm). The composition was then continuously stirred for 4 hours at 30° C. In the next step, the S/D mixture was removed by Castor oil extraction followed by hydrophobic chromatography as follows: The Castor oil extraction was carried out with 5% (w/w, final concentration) Castor oil (Henry Lamotte oils) by stirring the mixture for 25 minutes at 20° C. followed by incubation at 20° C. for 1 hour to allow phases separation. Two phases were formed, a lower aqueous phase comprising the fibrinogen and an upper oil phase comprising the S/D mixture. The lower phase was collected and filtered through 0.8+0.45 μm depth filter (Sartopore 2 300, Sterile Capsule, Sartorius). The filtrate was transferred through a C-18 column to remove the remaining S/D traces.

Pasteurization.

180% (w/w) sucrose and 11% (w/w) glycine were added into the solution as stabilizers during the pasteurization step. The composition was slowly stirred (50 rpm) for 10 hours at 58-60° C.

Buffer I Composition.

| Component | Concentration |
|---|---|
| 1  Sodium Chloride | 120 mM |
| 2  tri-Sodium Citrate | 10 mM |
| 3  Glycine | 120 mM |
| Titration to pH 7.4; components 4-5 were add before use. | |
| 4  2% Alhydrogel (Al(OH)$_3$) | 0.75 g per 30 g pellet |
| 5  TEA Sepharose gel* | 10 ml (settled resin)** per 30 g pellet |

*GE Healthcare, catalog Number 28-4109-03. TEA Sepharose gel was added into the buffer used for suspension of pieces 2 & 4 only (see procedure below).
**"Settled resin volume" - the volume of the resin after it was allowed to precipitate and the excess buffer was removed.

Buffer II Composition.

| Component | Concentration |
|---|---|
| 1  Sodium Chloride | 120 mM |
| 2  tri-Sodium Citrate | 10 mM |
| Titration to pH 7.4; components 3-5 were added before use. | |
| 3  Human Serum Albumin | 8 mg/ml |
| 4  2% Alhydrogel (Al(OH)$_3$) | 3.6 g per 120 g pellet |
| 5  TEA Sepharose gel* | 10 ml (settled resin)** per 120 g pellet |

*Added only in one treatment group (see procedure below).
**"Settled resin volume" - the volume of the resin after it was allowed to precipitate and the excess buffer was removed.

Buffer III Composition.

| | Component | Concentration |
|---|---|---|
| 1 | Sodium Chloride | 120 mM |
| 2 | tri-Sodium Citrate | 10 mM |
| 3 | Calcium chloride | 1 mM |

Titration to pH 7.0-7.2

Example 1

Removal of Plasmin(Ogen) from an Aluminum Hydroxide Precipitate Material Comprising Fibrinogen The aluminum hydroxide precipitate material that is a by-product in the course of FVIII purification (described in the material section), contains a great deal of fibrinogen. Therefore, this aluminum hydroxide precipitate can be used as a starting material for fibrinogen purification. However, this material usually comprises high concentrations of proteolytic enzymes e.g. plasmin(ogen) which may affect the stability of the fibrinogen macromolecule.

The aluminum hydroxide precipitate (pellet) was supplied as frozen block. The aim of the following experiment was to neutralize and remove the plasmin(ogen) as quickly as possible from this pellet to avoid degradation of the fibrinogen macromolecule throughout subsequent purification steps.

In the beginning of the purification process, it is of advantage to reduce the frozen mean particle size to maximize the contact surface area of the pellet to buffer solution to be used in a subsequent step. Therefore, the first approach was to produce 2-8 mm frozen pellet particles. Two different methods were tested to reduce the size of the particles: a manual grinding using scissors or a mechanical grinding using a blender (before each method, the size of the particles was manually reduced using a chisel and a hammer).

Typically, mechanical grinding is faster, produces uniform sized particles, and can be initiated at a lower temperature (as compared to the manual grinding)—minimizing the beginning of the lytic process, but on the other hand during the procedure itself heat may be generated and applied to the material and therefore harm the protein activity. In contrast, manual grinding is gentle, but is time consuming and may produce variable sized particles.

The next approach was to subject the 2-8 mm frozen particles containing fibrinogen to plasmin(ogen) removal. For this purpose, the ice particles were batch-wise exposed to immobilized tranexamic acid under specific conditions which allow formation of a heterogeneous mixture. The following parameters affect solubility of molecules: temperature, pH, and presence of organic solvents. The 2-8 mm frozen pellet particles were suspended in different solutions (with or without the immobilized tranexamic acid) in which these parameters were adjusted in order to obtain the heterogeneous mixture.

To initially create differential solubility of plasmin(ogen) and fibrinogen, the 2-8 mm frozen particles comprising the pellet of particles were suspended in a buffer comprising the immobilized tranexamic acid (Buffer I composition as specified in the materials and methods section) with the pH level adjusted to 7.2-7.3, the temperature was kept at 30-32° C., and the ethanol concentration was reduced from about 5% to about ~1% (as a result of buffer addition). This suspension step was carried out by incubation of 30 or 90 minutes. Following the suspension step the mixture was centrifuged and filtered for removal of the aluminum hydroxide, the immobilized inhibitor, and the captured plasmin(ogen) from the mixture.

To examine whether the obtained fibrinogen macromolecule was functional, fibrinogen concentration was measured by the Clauss clotting time method described in the materials and methods above.

The purification procedure was carried out specifically as elaborated below:

1. The pellet aluminum hydroxide precipitate starting material (prepared as described in the materials and methods section) was introduced into the purification process in the form of a solid frozen block, at −80° C. The frozen pellet was removed from the freezer and broken with a chisel and a hammer to obtain 4 frozen pieces of 30 g each (pieces of smaller than 5 cm). The frozen pieces were then transferred to a −20° C. freezer for approximately 1 hour and allowed to equilibrate to −20° C. Then, the material was incubated at room temperature (20-25° C.) for 15 minutes until the pieces reached a temperature of approximately 0° C.
2. In the next step, the size of the four pieces was reduced. Pieces 1 & 2 were grinded/minced (twice for 20 sec each time with a 40 sec interval) using a blender/grinding machine at the highest speed (Bar Blender, model 36BL74, Waring Commercial, CO, USA) and pieces 3 & 4 were cut with scissors. In both methods about 2-8 mm pieces were obtained. This step was carried out at room temperature.
3. Each of the four grinded/cut ice pieces of pellet was suspended in 120 ml pre-warmed (34° C.) suspension buffer (a ratio of 1:4 between the weight of the ice pieces and the volume of the suspension buffer). Two different buffers were used with (pieces 2 & 4) or without (pieces 1 & 3) TEA-Sepharose gel (see buffer components in the materials and methods section under "Buffer I composition"). Pieces 1 & 3 (without TEA-Sepharose gel in the buffer composition) were used as reference. The solutions were stirred on a magnetic stirrer device for 10 minutes while keeping the temperature at 30-32° C.
4. The pH was adjusted to 7.2-7.3 using 0.1 M NaOH.
5. The solution was then incubated while stirring at 30-32° C. for 30 minutes (suspension for duration of 30 minutes). The pH was monitored and adjusted to pH 7.2-7.3 using 0.1 M NaOH.
6. Half of each solution was transferred into a new tube and immediately processed according to the procedure elaborated below (from step 7 on). The rest was incubated for additional 60 minutes (a total suspension duration of 90 minutes including the 30 minutes incubation carried out in step 5) while stirring at 30-32° C. The pH was monitored every 30 min and adjusted with 0.1M NaOH to 7.2-7.3.
7. The solutions of all eight treatments* were centrifuged at 17,000 g for 25 min at 20° C. and the supernatant (comprising the fibrinogen) was transferred into a new tube. This step was carried out to remove the bulk of the aluminum hydroxide, the bulk of the TEA Sepharose gel and the captured plasmin(ogen).
8. The supernatant was filtered using a peristaltic pump through a pre-wetted (with the suspension buffer) 3 µm MidiCap filter (Sartorius, Sartopure; Cat. No. PP2#5595302P7-00-A). To prevent damage to the fibrinogen during the filtration, the pressure was kept below ≤0.2 bar by adjusting the pump speed.
9. An additional filtration was performed using a 1.2 µm MidiCap glass fiber (GF) filter (Sartorius, Sartopure GF+; Cat. No. #5555303P7-00-A). The two filtration steps resulted in maximal removal of aluminum hydroxide, TEA-Sepharose gel and captured lytic enzyme residues. The first filtration step (through the 3 nm filter) was carried out to avoid blockage of the 1.2 µm filter.
10. For stabilization, 0.1 M $CaCl_2$ was added to a final concentration of 1 mM.

The eight treatments were—treatment 1: mechanically grinded pellet; treatment 2: mechanically grinded pellet and treated with immobilized TEA; treatment 3: manually grinded pellet; treatment 4: manually grinded pellet and treated with immobilized TEA. Each of treatments 1-4 were suspended and incubated for duration of 30 or 90 minutes.

The fibrinogen concentration was then measured in the different eight groups in two time points: at the end of step 10 (T0) and 4 days following incubation at room temperature (20-25° C.; T4). Fibrinogen concentration was measured by the Clauss clotting time method as described in the materials and methods section. The results are shown in Table 1.

TABLE 1

Fibrinogen concentration in the different treatments at the different time points.

| | | Duration of suspension (min) | | | |
| | | 30 | | 90 | |
| | | Fibrinogen Concentration (mg/ml) | | | |
| | | Incubation time (days) | | | |
| Treatment | | T0 | T4 | T0 | T4 |
| --- | --- | --- | --- | --- | --- |
| 1 | Mechanical (Blender) | 35.3 | 0 | 36.8 | 9.3 |
| 2 | Mechanical (Blender) + immobilized TEA | 40.2 | 23.0 | 57.6 | 27.5 |
| 3 | Manual (Scissors) | 17.3 | 2.2 | 42.2 | 1.6 |
| 4 | Manual (Scissors) + immobilized TEA | 25.8 | 11.9 | 44.6 | 25.5 |

* Both the mechanical and the manual methods included a preceding step of manually reducing the mean particle size using a chisel and a hammer (see step 1 of the purification procedure above).

In groups 1 and 3 it was observed that upon solubilization of the pellet with buffer alone, the fibrinogen was almost completely degraded on T4. Therefore, it is critical to neutralize the lytic enzymes during the step of solubilization. As observed in groups 2, 4 this degradation was controlled by the addition of immobilized TEA.

It was also observed that reducing the mean particle size by a mechanical method combined with addition of immobilized TEA gave better results (Table 1 treatment 2 vs. 4).

More specifically, it was observed that treatment 2 (i.e. mechanical reduction in the particle's size and suspension for 30 or 90 minutes in the presence of an immobilized inhibitor) resulted in increased fibrinogen concentration at T0 and T4 as compared to the other treatments (treatments 1, 3, and 4). Comparison between the two suspension periods (30 vs. 90) of treatment 2 shows that the prolonged suspension period (90 min) resulted in increased fibrinogen concentration as compared to the shorter period (30 min) at both time points (27.5 compared to 23.0 mg/ml at T4; and 57.6 compared to 40.2 mg/ml at T0).

Also, it was observed that addition of immobilized inhibitor into the suspension buffer resulted in an increased fibrinogen concentration at both time points as compared to the control group without immobilized inhibitor (compare treatment 2 with treatment 1, and treatment 4 with treatment 3).

It was therefore found that in order to obtain a functional fibrinogen macromolecule, it is beneficial to add immobilized inhibitor into the suspension buffer while creating differential solubility between the fibrinogen and the plasmin(ogen). Advantageously, in order to further increase the functionality, the particles of the material can be reduced by mechanical means e.g. to a mean particle size of 2-8 mm (a preceding manual reduction in the mean particle size to <5 cm can be carried out) prior to suspension and the suspension may be carried out for a prolonged period of time (such as longer than 30 minutes).

In treatment 2 with a 90 min. incubation, approximately 80% of the plasmin(ogen) was removed from the precipitate.

The following experiment was carried out to verify the previous results and examine the effect of the method used to reduce the mean size of the particles prior to the suspension step (mechanical vs. manual grinding as a second step of reducing the particle's size) and the duration of the suspension step (30 vs. 90 minutes) on the functionality of the obtained fibrinogen macromolecule. In this experiment all treatment groups were suspended in the presence of an immobilized inhibitor.

The procedure was carried out as elaborated in steps 1-10 above subjected to the following modifications:

1) Only two frozen pieces were obtained in step 1, one was grinded using a blender machine and the other was cut with scissors; 2) Both frozen pieces, were suspended in step 3 in a buffer which included TEA-Sepharose gel (suspension buffer I was used as listed in the materials and methods section except that only 7 ml settled resin per 30 g of the pellet was used); 3) In step 9, filtration was carried out using 1 μm Ultipor GF+ filter (PALL, Cat. No. U010Z047050) instead of 1.2 μm.

Fibrinogen concentration was measured at the different groups at T0 (in the end of the processes) and 3 days following incubation at room temperature (20-25° C.; T3). The measurement was carried out as described above.

TABLE 2

Fibrinogen concentration in the different settings at the different time points.

| | | Duration of suspension (min) | | | |
|---|---|---|---|---|---|
| | | 30 | | 90 | |
| | | Fibrinogen concentration (mg/ml) | | | |
| | | Incubation time (days) | | | |
| Treatment | | T0 | T3 | T0 | T3 |
| 1 | Mechanical (Blender) | 25.4 | 19.5 | 27.9 | 24.2 |
| 2 | Manual (Scissors) | 21.6 | 19.0 | 21.3 | 7.2 |

The results confirm the previous results and show that advantageously reducing the frozen mean particle size using a mechanical method (in addition to a preceding manual reduction in the mean particle size using a chisel and a hammer) combined with a prolonged suspension duration (e.g. 90 minutes) in the presence of an immobilized inhibitor advantageously results in an increased fibrinogen concentration (see fibrinogen concentration at T0 and T3 at 90 min suspension period of treatment 1 as compared to the parallel treatment groups).

A scale up experiment was carried out with 120 g frozen pellet. In this experiment, the particle size reduction of all treatment groups was carried out by mechanical means and a prolonged suspension was carried out (90 minutes). This experiment included two treatment groups: suspended with or without an immobilized inhibitor.

The experiment was carried out in the same manner as elaborated above except that: (1) Frozen pieces of 120 g were prepared (see step 1 in the above elaborated procedure) and suspension in step 3 was carried out in 480 ml pre-heated (34° C.) buffer (as above—a ratio of 1:4 between the weight of the ice pieces and the volume of the suspension buffer); (2) Particle size reduction was carried out by a blender machine (as elaborated in step 2 above); (3) Buffer II composition was used in step 3 (for suspension) and 8 (for wetting the pump); (4) Only a suspension period of 90 minutes was carried out; (5) Stabilization (step 10 above) was carried out also by adding glycine to a final concentration of 120 mM (in the previous procedure glycine was included in the suspension buffer, thus not added at the stabilization step). In this experiment additional production steps were carried out (in addition to the above mentioned 1 to 10 steps) as elaborated below.

Biological materials administered to humans must be subjected to virus inactivation steps in order to minimize the potential risk posed by blood-borne pathogens. Thus, the obtained composition was subjected to two viral inactivation steps: solvent/detergent (S/D) treatment which inactivates lipid-enveloped viruses; and pasteurization by which heat destroys both lipid-enveloped and non-enveloped viruses (both treatments are specified in the materials and methods section). In the next step, the virally inactivated composition was diluted with 2.5 weights (to reduce viscosity) of buffer (see Buffer III composition above) and filtrated through 3 μm filter (Sartopure PP2, Sartorius) in order to remove gross particles. The stabilizers (sucrose and glycine added at the pasteurization step) were removed from the solution by ultrafiltration/diafiltration against buffer III using cassettes of pore size 100 K (Pall). The resulted homogenous solution was subjected to column purification using a TEA-Sepharose column (GE healthcare) to remove the remaining plasmin(ogen) from the solution as described in EP 1390485. The solution was then concentrated by ultrafiltration [using cassettes of pore size 100 K (Pall)] to a concentration of 80-120 mg/ml total protein and formulated with glycine (added to a concentration of 120 mM), and arginine hydrochloride (added to a concentration of 2%).

Figure 1:
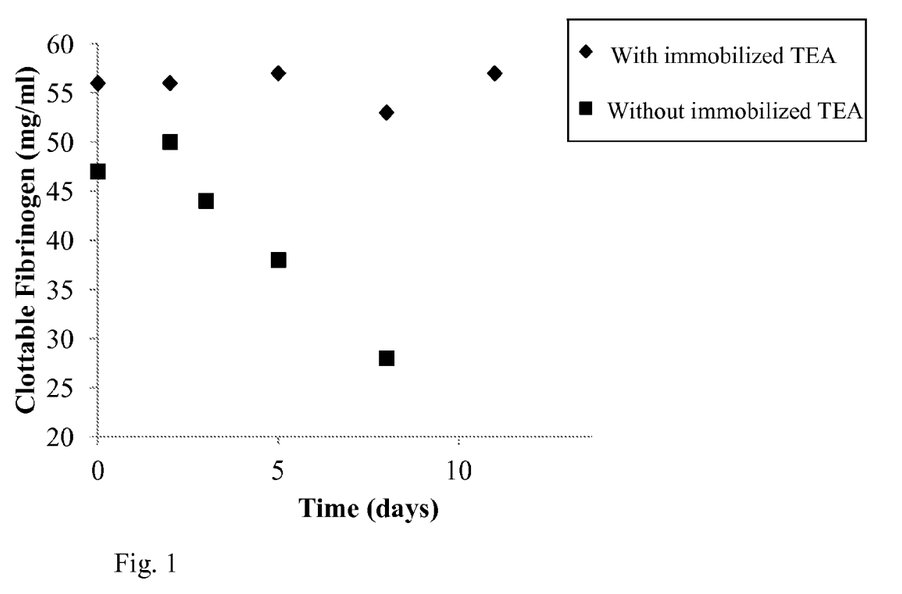
FIG. 1 shows clottable fibrinogen concentration in the course of time of two fibrinogen containing samples that were purified from an aluminum hydroxide precipitate which comprises the proteolytic enzyme plasmin and/or plasminogen. The samples were treated with or without immobilized tranexamic acid (TEA) during the purification process.

Fibrinogen concentration was measured in the different groups (with or without immobilized inhibitor in the suspension buffer) at T0 (in the end of the production process) and 2, 3, 5, 8 and 11 days following incubation at room temperature (20-25° C.). The results are shown in Table 3 and in FIG. 1.

TABLE 3

Fibrinogen concentrations in the course of time in samples treated with or without immobilized TEA-Sepharose gel at the suspension step.

| Treatment at suspension step | Fibrinogen Concentration (mg/ml)** Incubation Time (days) | | | | | |
|---|---|---|---|---|---|---|
| | 0 | 2 | 3 | 5 | 8 | 11 |
| With immobilized TEA-Sepharose | 56 | 56 | *ND | 57 | 53 | 57 |
| Without immobilized TEA-Sepharose | 47 | 50 | 44 | 38 | 28 | *ND |

*ND—Not Determined.
**One sample was tested at each time point. Each sample was read twice.

The results are concordant with the previous results and show that adding an immobilized-TEA at the suspension step resulted in increased fibrinogen concentration at T0 (i.e. increased fibrinogen yield) as compared to treatment lacking immobilized-TEA at the suspension step.

In addition, samples treated with immobilized-TEA at the suspension step exhibited increased stability as compared to samples that were not subjected to immobilized-TEA at the suspension step. For example, no substantial reduction was observed in the fibrinogen concentration in the course of time in samples treated with immobilized TEA-Sepharose gel during the suspension step even 11 days after incubation at room temperature. Whereas, samples that were not treated with immobilized TEA-Sepharose gel at the suspension step exhibited approximately 40% reduction in fibrinogen concentration after 8 days.

Figure 2:
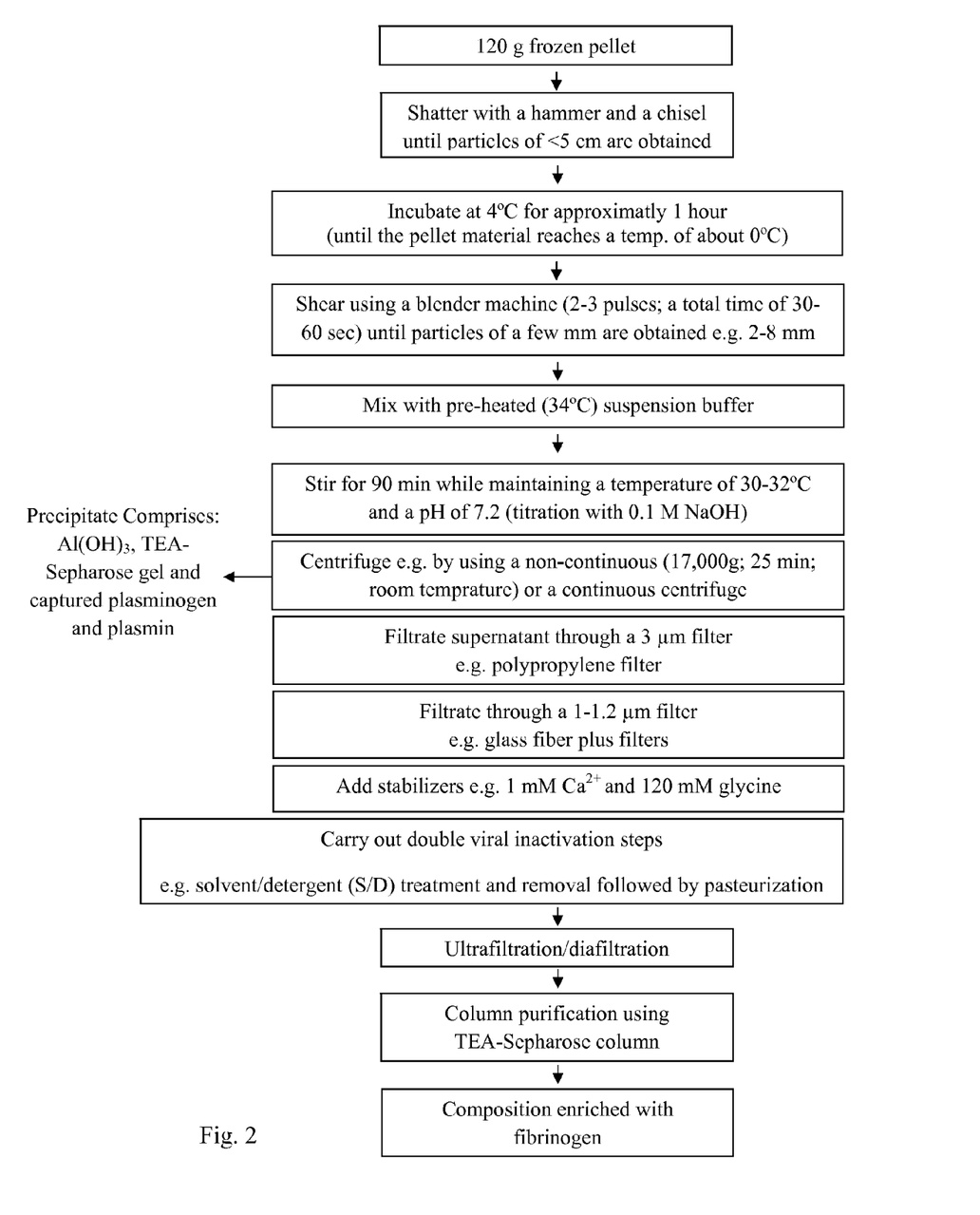
FIG. 2 is a flow chart showing one embodiment of a method for fibrinogen enrichment including removal of plasmin and plasminogen (the lytic enzyme) from an aluminum hydroxide precipitate material. TEA immobilized on sepharose gel was used as the inhibitor. The precipitate material was provided in a frozen form. The composition of the suspension buffer used was: 480 ml buffer (7 g NaCl; 2.95 g tri-sodium citrate dehydrate; 8 mg/ml Human Serum Albumin; and pure water to 1 Liter; pH=7.4); 6-40 ml settled TEA-Sepharose; and 3.6 g of 2% $Al(OH)_3$; at pH 7.4.

FIG. 2 shows a flow chart of embodiment steps for removal of plasmin and plasminogen (the lytic enzyme) from an aluminum hydroxide precipitate material comprising fibrinogen (the macromolecule). Tranexamic acid immobilized on sepharose gel was used as the inhibitor and was added into the suspension buffer. The precipitate material was provided in a frozen form. The composition of the suspension buffer used was: 480 ml buffer (7 g NaCl; 2.95 g tri-sodium citrate dehydrate; 8 mg/ml Human Serum Albumin; and pure water to 1 Liter; pH=7.4); 6-40 ml settled TEA-Sepharose; and 3.6 g of 2% Al(OH)$_3$; at pH 7.4.

What is claimed is:

1. A method for removing a lytic enzyme from a precipitated biological mixture, the biological mixture comprising the lytic enzyme capable of degrading fibrinogen, fibrinogen and aluminum hydroxide particles, the method comprising the steps of:

providing the precipitated biological mixture;
providing an inhibitor of the lytic enzyme immobilized on a carrier;
partially dissolving the precipitated biological mixture with an aqueous solution under conditions that allow the lytic enzyme to dissolve to obtain a heterogeneous mixture comprising dissolved lytic enzyme and solid particles including fibrinogen and aluminum hydroxide particles;
contacting the heterogeneous mixture with the immobilized inhibitor in batch form followed by a step of fully dissolving the fibrinogen solid particles in the mixture thereby obtaining a mixture including immobilized inhibitor, aluminum hydroxide particles and fully dissolved fibrinogen; and
separating the aluminum hydroxide and the immobilized inhibitor and the lytic enzyme bound to the inhibitor from the fully dissolved fibrinogen by centrifugation and/or filtration, wherein the partially dissolving conditions are selected from the group consisting of a pH range of 7.2-7.3, a temperature range of 30-32C, an ethanol concentration in the range of 0.2 to 5%, and a combination thereof.

2. The method according to claim 1, wherein the partially dissolving conditions comprise a pH range of 7.2-7.3, a temperature range of 30-32° C., and an ethanol concentration in the range of 0.2 to 5%.

3. The method according to claim 1, wherein the precipitated biological mixture derives from a blood fraction.

4. The method according to claim 1, wherein the precipitated biological mixture is a by-product precipitate from the manufacture process of factor VIII.

5. The method according to claim 1, wherein the lytic enzyme is a protease.

6. The method according to claim 1, wherein the inhibitor is an amino acid analog.

7. The method according to claim 1 wherein the macromolecule is fibrinogen, the lytic enzyme is plasmin and/or plasminogen, and the inhibitor is a lysine analog.

8. The method according to claim 7, wherein the lysine analog is tranexamic acid.

9. The method according to claim 1, wherein the precipitated biological mixture is provided frozen.

10. The method according to claim 9, further comprising the step of reducing the mean particle size of the frozen precipitated biological mixture to about 2-8 mm.

11. The method according to claim 10, wherein the reduction in the mean particle size is carried out mechanically.

12. The method according to claim 11, wherein the reduction in the mean particle size is carried out using a blender machine.

13. The method according to claim 1, wherein the contacting step is carried out for more than 30 minutes.

14. The method according to claim 1, wherein the separating step is carried out by centrifugation and/or filtration.

15. The method according to claim 1, wherein the steps of partially dissolving the precipitated biological mixture and contacting the heterogeneous mixture with the immobilized inhibitor are carried out simultaneously.

* * * * *